(12) United States Patent
Tets et al.

(10) Patent No.: US 10,584,095 B2
(45) Date of Patent: Mar. 10, 2020

(54) METHOD OF PRODUCING A SODIUM SALT OF (2,6-DICHLOROPHENYL)AMIDE CARBOPENTOXYSULFANILIC ACID

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Viktor Iosifovich Krutikov, St. Petersburg (RU)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 0 days.

(21) Appl. No.: 15/758,410

(22) PCT Filed: Sep. 13, 2016

(86) PCT No.: PCT/RU2016/000624
§ 371 (c)(1),
(2) Date: Mar. 8, 2018

(87) PCT Pub. No.: WO2017/048156
PCT Pub. Date: Mar. 23, 2017

(65) Prior Publication Data
US 2018/0244612 A1    Aug. 30, 2018

(30) Foreign Application Priority Data

Sep. 15, 2015   (RU) ................................ 2015141264

(51) Int. Cl.
*C07C 315/04*    (2006.01)
*C07C 311/44*    (2006.01)
(Continued)

(52) U.S. Cl.
CPC .......... *C07C 315/04* (2013.01); *C07C 303/38* (2013.01); *C07C 311/21* (2013.01); *C07C 311/44* (2013.01); *C07C 317/42* (2013.01)

(58) Field of Classification Search
None
See application file for complete search history.

(56) References Cited

U.S. PATENT DOCUMENTS 6,417,181 B1   7/2002   Bender et al.
6,569,864 B1   5/2003   Douglas et al.
(Continued)

FOREIGN PATENT DOCUMENTS

DE    3544409 A1    10/1986
DE   10210319 A1     9/2003
(Continued)

OTHER PUBLICATIONS

International Search Report issued by the International Searching Authority in International Application No. PCT/RU2016/000624 dated Mar. 6, 2017.
(Continued)

*Primary Examiner* — Amy C Bonaparte
(74) *Attorney, Agent, or Firm* — Troutman Sanders LLP

(57) ABSTRACT

The invention relates to the field of organic chemistry and medicine, and more particularly to a method of producing synthetic biologically active derivatives of carbopentoxysulfanilic acid. The present method of producing a sodium salt of (2,6-dichlorophenyl)amide carbopentoxysulfanilic acid is characterized in that the reaction mass formed during the production of (2,6-dichlorophenyl)amide carbopentoxysulfanilic acid is agitated in a medium which is acidified with a solution of hydrochloric acid to pH 5-5.5, and the isolated precipitate may be washed with water acidified with a solution of hydrochloric acid to pH 5-5.5. This increases
(Continued)

the yield of a sodium salt of (2,6-dichlorophenyl)amide carbopentoxysulfanilic acid to 70% (compared to a prior art yield of 32%) and also increases the purity of the target sodium salt.

8 Claims, 3 Drawing Sheets

(51) Int. Cl.
  *C07C 303/38* (2006.01)
  *C07C 311/21* (2006.01)
  *C07C 317/42* (2006.01)

(56) References Cited

U.S. PATENT DOCUMENTS

| | | | |
|---|---|---|---|
| 9,567,295 | B2 * | 2/2017 | Tets ................ C07C 317/32 |
| 2003/0086992 | A1 | 5/2003 | Tanaka et al. |
| 2004/0157848 | A1 | 8/2004 | Maziasz |
| 2005/0037032 | A1 | 2/2005 | Catania et al. |
| 2013/0287841 | A1 | 10/2013 | Tets et al. |

FOREIGN PATENT DOCUMENTS

| | | |
|---|---|---|
| EP | 1038868 A2 | 9/2000 |
| EP | 1136472 A1 | 9/2001 |
| EP | 2659891 A1 | 11/2013 |
| RU | 1405269 A1 | 12/1993 |
| RU | 2182828 C1 | 5/2002 |
| RU | 2199526 C2 | 2/2003 |
| RU | 2373951 C1 | 11/2009 |
| RU | 2452490 C1 | 6/2012 |
| WO | 2000/034234 A1 | 6/2000 |
| WO | 2012/091610 A1 | 7/2012 |

OTHER PUBLICATIONS

Written Opinion issued by the International Searching Authority in International Application No. PCT/RU2016/000624 dated Mar. 6, 2017.

Berge, S.M. et al., "Pharmaceutical Salts" Journal of Pharmaceutical Sciences (1977) vol. 66, Issue 1, pp. 1-19.

Didkovskii et al., "Gerpes~virusnaya infekstiya: Klinicheskoe znachenie I printsipy terapii (Herpes Virus Infection: Clinical Significance and Principles of Therapy)" Russkii Meditsinskii Zhurnal (2004) vol. 12, No. 7, pp. 459-464.

English translation (2014) of RU 2199526 (2003), 6 pages total.

Extended European Search Report issued in European Application No. 11853372.8, dated Dec. 10, 2013.

Furman et al., "Aciclovir-resistant mutants of herpes simplex virus typr 1 express altered DNA polymerase or reduced aciclovir phosphorylating activities" J. Virol. (1981) vol. 3, pp. 936-941.

International Preliminary Report on Patentability issued in International Application No. PCT/RU2014/000420 dated Oct. 12, 2015 and English Translation thereof, 9 pages.

International Preliminary Report on Patentability issued by the International Searching Authority in International Application No. PCT/RU2016/000624, dated Mar. 20, 2018.

International Preliminary Report on Patentability issued in corresponding International Application No. PCT/RU2011/000060 dated Jul. 2, 2013. (translation included).

International Search Report and Written Opinion dated Sep. 25, 2014, issued in International Application No. PCT/RU2014/000420. (translation included).

International Search Report and Written Opinion dated Sep. 29, 2011, issued in International Application No. PCT/RU2011/000060. (translation included).

Mashkovskiy, Lekarstvenniye Sredstva, Moscow (2001) vol. 2, pp. 321-334.

Noueiry, A.O. et al., "Identification of Novel Small-Molecule Inhibitors of West Nile Virus Infection" Journal of Virology (2007) vol. 81, No. 21, pp. 11992-12004.

Pharmaceutical Salts: Properties, Selection, and Use (p. 331 )(Stahl et al., Ed.)(2002).

Rothaus, "Genital Herpes" (NEJM Resident 360 (Aug. 18, 2016))(retrieved from <https://resident360.nejm.org/content_items/genital-herpes> on Jun. 24, 2017), 3 pages total.

Supplemental/Extended European Search Report issued in European Patent Application No. 14806838.0 dated Jan. 13, 2017, 9 pages.

* cited by examiner

METHOD OF PRODUCING A SODIUM SALT OF (2,6-DICHLOROPHENYL)AMIDE CARBOPENTOXYSULFANILIC ACID

CROSS-REFERENCE TO RELATED APPLICATIONS

This application is a U.S. National Phase of International Patent Application No. PCT/RU2016/000624, filed on Sep. 13, 2016, which published as WO 2017/048156 A1 on Mar. 23, 2017 and claims priority to Russian Patent Application No. 2015141264, filed on Sep. 15, 2015, all of which applications are herein incorporated by reference in their entirety.

TECHNICAL FIELD

The invention relates to the field of organic chemistry and medicine, in particular to a method for the preparation of synthetic biologically active derivatives of carbopentoxysulfanilic acid, specifically to a process for the preparation of the sodium salt of (2,6-dichlorophenyl)amide of carbopentoxysulfanilic acid, which has a pronounced antiviral activity mostly against various viruses of the herpes family (Herpesviridae), and can be used in medicine, veterinary and cosmetology for the prevention and treatment of diseases associated with the herpes family viruses.

BACKGROUND ART

A method for the preparation of the (2,6-dichlorophenyl)amide of carbopentoxysulfanilic acid by a four-step synthesis is known from the prior art (see RU 2452490 C1, publ. Oct. 6, 2012):

Stage 1

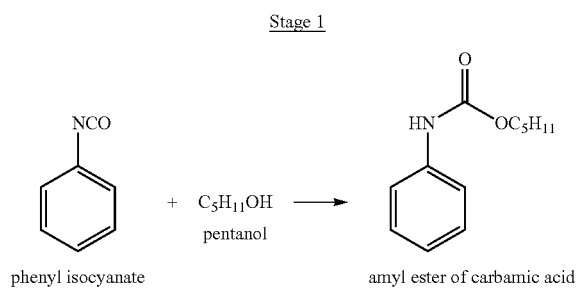

phenyl isocyanate    amyl ester of carbamic acid

Amyl ester of carbamic acid is synthesized. Phenyl isocyanate (11.5 g-0.096 mol) is mixed with pentanol (amyl alcohol) (8.5 g-0.096 mol), the reaction mass is heated, and after 1 hour the mixture solidifies in the form of colorless crystals. The yield of amyl ester of carbamic acid is about 100%.

Stage 2

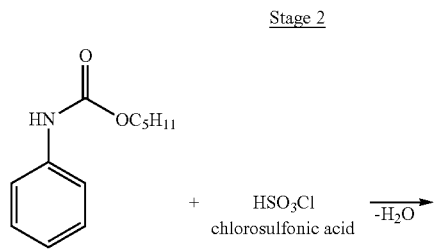

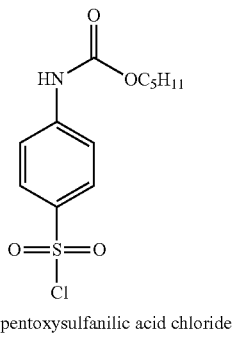

carbopentoxysulfanilic acid chloride

Carbopentoxysulfanilic acid chloride is synthesized. To chlorosulfonic acid (17.5 g to 0.150 mol) heated to 30° C., amyl ether of phenylcarbamic acid (2.07 g-0.010 moles) is slowly added while stirring, maintaining the temperature of the reaction mass at a level no higher than 35° C. Then the mixture is slowly heated to 50° C. and kept at a temperature of 50-55° C. for 2 hours. The resulting sulphomass is poured onto ice while stirring, keeping the temperature below 20° C. The precipitate is filtered off, washed with ice water up to the pH of filtrate 7, dried in air and then in a desiccator. The yield of carbopentoxy sulfanilic acid chloride is about 100%.

Stage 3

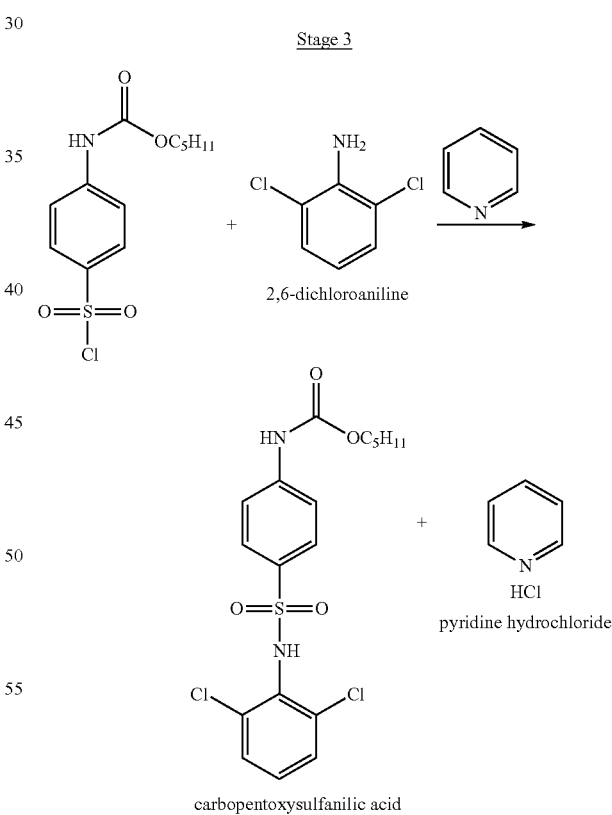

carbopentoxysulfanilic acid (2,6-dichlorophenyl)amide of carbopentoxysulfanilic acid is synthesized. To a mixture of 2,6-dichloroaniline (2.2 g to 0.0136 mol) and pyridine (3.23 g-0.0406 mol) carbopentoxysulfanilic acid chloride (6.2 g-0.0203 mol) is added in portions at the temperature of 85° C.; the reaction mass is stirred at 80° C. for 45 minutes. Then 20 ml of hot water are added to the mass, the mixture is acidified with hydrochloric acid to pH 3-4 and cooled to the room temperature. The resulting precipitate is filtered off, washed with water until the odor of pyridine disappears, and dried. After recrystallization, the yield of (2,6-dichlorophenyl)amide of carbopentoxysulfanilic acid is about 40%.

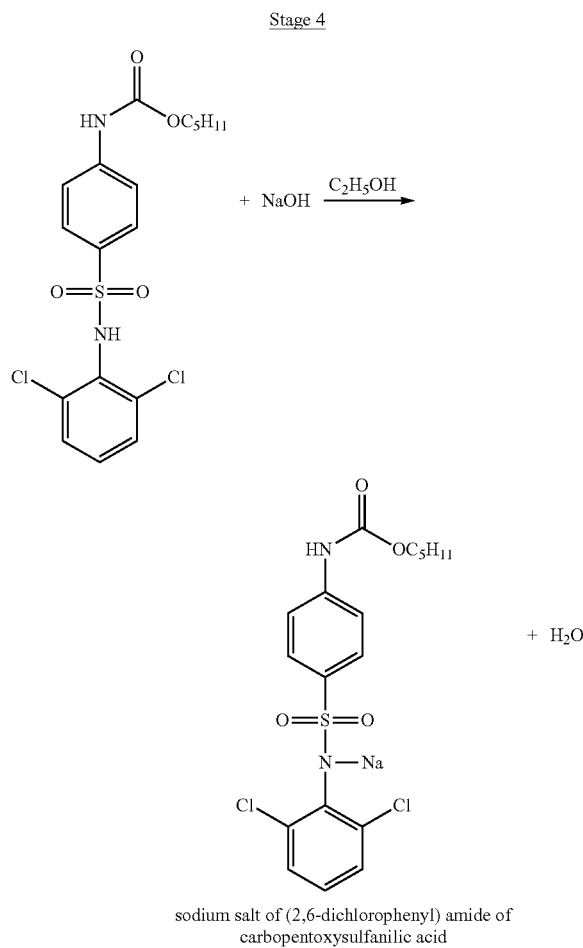

sodium salt of (2,6-dichlorophenyl) amide of carbopentoxysulfanilic acid

The final product, the sodium salt of (2,6-dichlorophenyl) amide of carbopentoxysulfanilic acid is synthesized. 0.232 g of sodium hydroxide (NaOH) are dissolved in 5 ml of ethyl alcohol ($C_2H_5OH$), and 2.5 g of (2,6-dichlorophenyl)amide of carbopentoxysulfanilic acid are dissolved in 30 ml of ethyl alcohol ($C_2H_5OH$). Then, the two solutions are mixed and stirred for 20 minutes, after which the ethyl alcohol is distilled off under vacuum. The remaining precipitate is dried. The product yield was 2.1 g (80%). As a result of the process, the sodium salt of (2,6-dichlorophenyl)amide of carbopentoxysulfanilic acid is obtained.

The disadvantage of this method, accepted as the prototype of the present invention, is the low overall yield of the final product, sodium salt of (2,6-dichlorophenyl)amide of carbopentoxysulfanilic acid, which does not exceed 32% as yields of the intermediate products and the final product at individual stages are 100, 100, 40 and 80%, respectively. Thus, the total yield of sodium salt of (2,6-dichlorophenyl) amide of carbopentoxysulfanilic acid does not exceed 32%.

SUMMARY OF THE INVENTION

It is an object of the present invention to increase the yield and the purity of the target sodium salt of (2,6-dichlorophenyl)amide of carbopentoxysulfanilic acid.

According to the invention, in the method of preparation of the sodium salt of (2,6-dichlorophenyl)amide of carbopentoxysulfanilic acid that includes synthesis of (2,6-dichlorophenyl)amide of carbopentoxysulfanilic acid by mixing 2,6-dichloroaniline and pyridine, then adding carbopentoxysulfanilic acid chloride to the mixture, mixing of the reaction mass in a medium acidified with a solution of hydrochloric acid, segregation of the precipitate, its washing and drying, and subsequent synthesis of the sodium salt of (2,6-dichlorophenyl)amide of carbopentoxysulfanilic acid by mixing the solutions in ethanol of sodium hydroxide and (2,6-dichlorophenyl)amide of carbopentoxysulfanilic acid, stirring the resulting mixture, distilling off the ethanol and drying the precipitate; the reaction mass in the preparation of (2,6-dichlorophenyl)amide of carbopentoxysulfanilic acid is stirred in a medium acidified with a solution of hydrochloric acid to a pH of 5-5.5.

As a result of the process, the sodium salt of (2,6-dichlorophenyl)amide of carbopentoxysulfanilic acid is obtained, which has the following general formula:

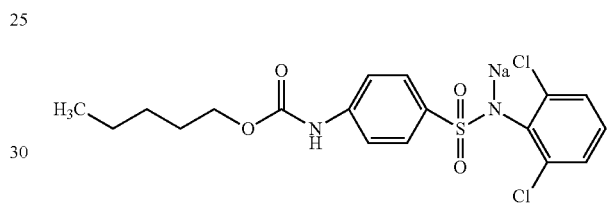

When using the claimed process for the preparation of the sodium salt of (2,6-dichlorophenyl) amide of carbopentoxysulfanilic acid, its yield increased to 56% (for comparison, in the prototype the yield is 32%) due to the creation of a medium with a pH of 5-5.5 when obtaining (2,6-dichlorophenyl)amide of carbopentoxysulfanilic acid corresponding to the dissociation constant of the reaction mass at which the substance precipitates more completely.

Predominantly, washing of the precipitate can be carried out with water acidified with a solution of hydrochloric acid to a pH of 5-5.5. This ensures complete purification of the product from the excess of pyridine, while the excess of hydrochloric acid is successfully removed during subsequent crystallization.

The applicant is not aware of any sources of information that would contain information about identical technical solutions, which makes it possible to conclude that the claimed invention complies with the "Novelty" ("N") criterion.

Due to the implementation of the claimed technical solution, the technical result is achieved that is to increase the yield and the purity of the target (2,6-dichlorophenyl)amide of carbopentoxysulfanilic acid.

The applicant has not found any sources of information containing data on the effect of the distinctive features of the invention on the technical result achieved due to their implementation. This, according to the applicant, demonstrates the compliance of this technical solution with the condition of patentability "Inventive Step" ("IS").

BRIEF DESCRIPTION OF THE DRAWINGS

In the following, the invention will be explained with a detailed description of examples of its implementation with reference to the drawings, which specify the following.

PREFERRED EMBODIMENT

Figure 1:
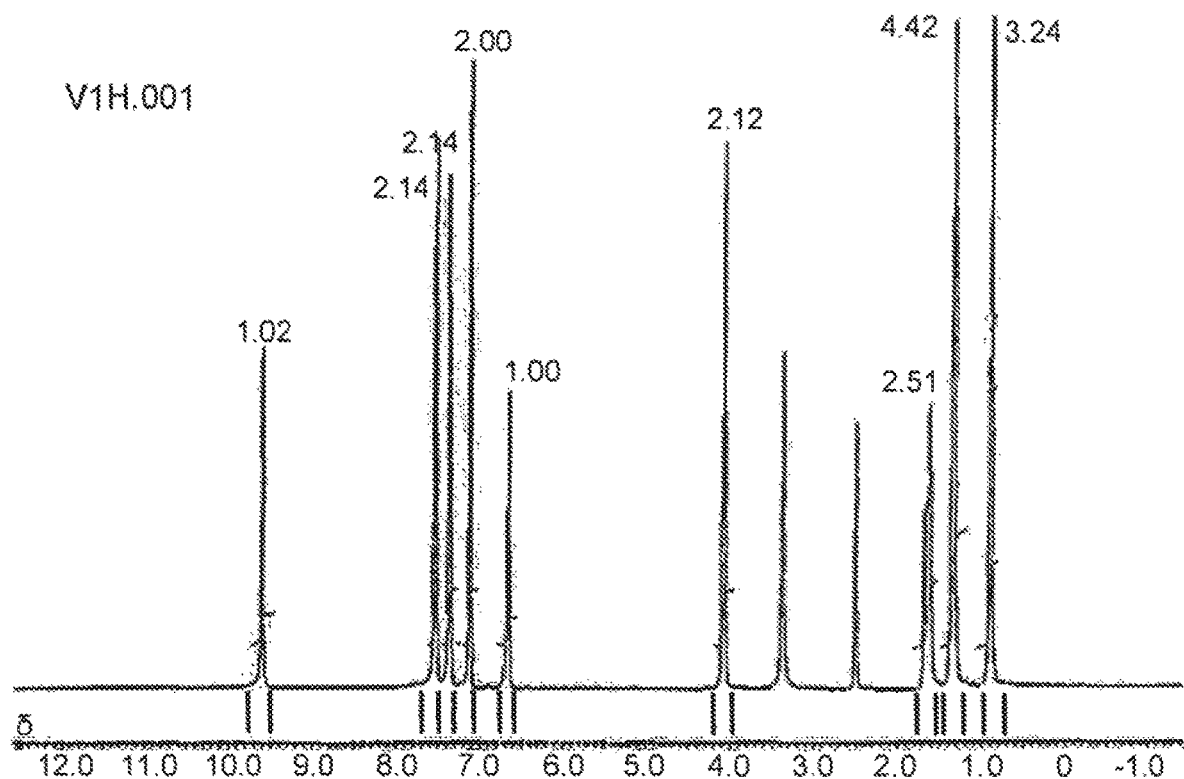
FIG. 1 shows the proton magnetic resonance spectrum of the sodium salt of (2,6-dichlorophenyl) amide of carbopentoxysulfanilic acid.

The preparation of the sodium salt of (2,6-dichlorophenyl) amide of carbopentoxysulfanilic acid by the method of the invention is illustrated by an example.

Phenyl isocyanate (11.5 g-0.096 mol) was mixed with pentanol (amyl alcohol) (8.5 g-0.096 mol), the reaction mass was heated, and after 1 hour the mixture solidified in the form of colorless crystals. Amyl ester of carbamic acid was obtained; the yield was about 100%.

To chlorosulfonic acid (17.5 g to 0.150 mol) heated to 30° C., amyl ether of phenylcarbamic acid (2.07 g-0.010 moles) was slowly added while stirring, maintaining the temperature of the reaction mass at a level no higher than 35° C. Then the mixture was slowly heated to 50° C. and kept at a temperature of 50-55° C. for 2 hours. The resulting sulpho-mass was poured onto ice while stirring, keeping the temperature below 20° C. The precipitate was filtered off, washed with ice water up to the pH of filtrate 7, dried in air and then in a desiccator. Carbopentoxy sulfanilic acid chloride was obtained as a result; the yield was about 100%.

To a mixture of 2,6-dichloroaniline (2.2 g to 0.0136 mol) and pyridine (3.23 g-0.0406 mol) carbopentoxysulfanilic acid chloride (6.2 g-0.0203 mol) was added in portions at the temperature of 85° C.; the reaction mass was stirred at 80° C. for 45 minutes. Then 20 ml of hot water were added to the mass, the mixture was acidified with hydrochloric acid to pH 5-5.5 and cooled to the room temperature. The resulting precipitate was filtered off, washed with water acidified with hydrochloric acid solution to a pH of 5-5.5, until the odor of pyridine disappeared, and dried. After recrystallization, the yield of the resulting (2,6-dichlorophenyl)amide of carbopentoxysulfanilic acid was 4.4 g-70%.

Further, 0.232 g of sodium hydroxide (NaOH) were dissolved in 5 ml of ethyl alcohol ($C_2H_5OH$), and 4.4 g of (2,6-dichlorophenyl)amide of carbopentoxysulfanilic acid were dissolved in 30 ml of ethyl alcohol ($C_2H_5OH$). Then, the two solutions were mixed and stirred for 20 minutes, after which the ethyl alcohol was distilled off under vacuum. The remaining precipitate was dried. The final product, the sodium salt of (2,6-dichlorophenyl)amide of carbopentoxysulfanilic acid, was obtained; the yield of the product was 3.6 g-80%.

The yields of the intermediate products and the final product at the individual stages were 100, 100, 70 and 80%, respectively. Thus, the total yield of sodium salt of (2,6-dichlorophenyl)amide of carbopentoxysulfanilic acid was 56%.

The individuality of the target product is proved by thin-layer chromatography on Silufol UV-254 plates, carbon tetrachloride-isopropanol eluent=2:1. No impurities were detected.

The structure of the synthesized product is proved by the methods of proton magnetic resonance (NMR), ultraviolet (UV) and infrared (IR) spectroscopy.

The characteristic signals in the NMR spectrum are the singlet of NH group in the range of 9.7 ppm and the multiplet in the range of 6.5÷7.5 ppm (FIG. 1).

Figure 2:
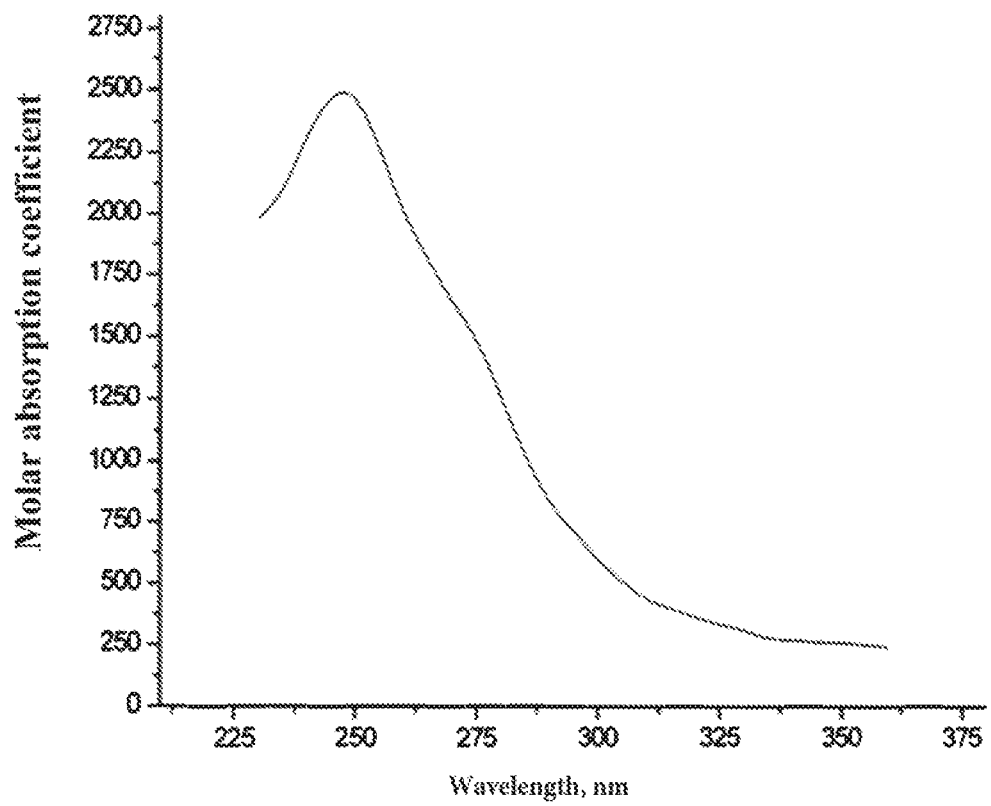
FIG. 2 shows the ultraviolet spectrum of the sodium salt of (2,6-dichlorophenyl) amide of carbopentoxysulfanilic acid.

The ultraviolet absorption spectrum of the solution obtained in the range from 200 to 380 nm has a maximum of 247±2 nm with an arm of (275±2 nm) (FIG. 2).

Figure 3:
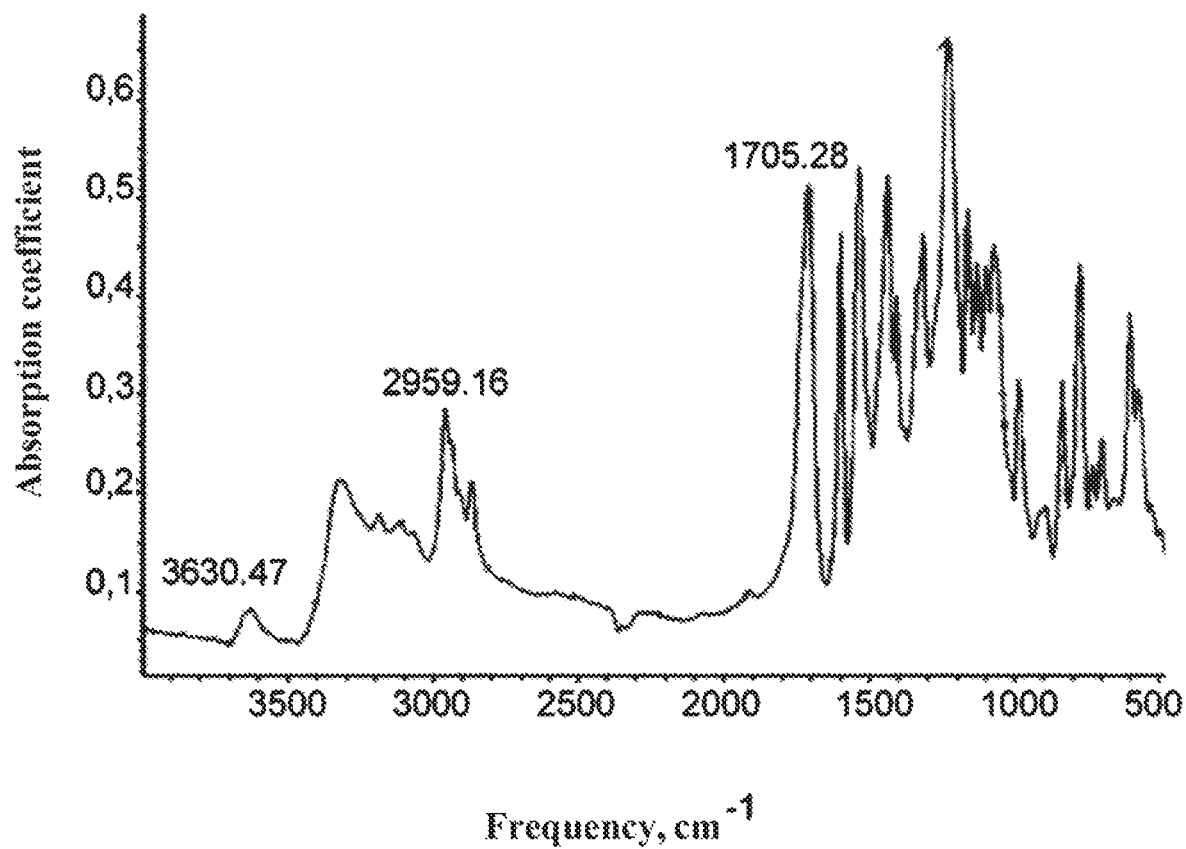
FIG. 3 shows the infrared spectrum of the sodium salt of (2,6-dichlorophenyl) amide of carbopentoxysulfanilic acid.

The characteristic absorption bands in the IR spectrum are shown in FIG. 3 (vibrations of the C—H bond in the $3600^{cm-1}$ range, NH in the 2900 $cm^{-1}$ range, C=O-1700 $cm^{-1}$).

INDUSTRIAL APPLICABILITY

The invention is implemented using common materials and equipment, resulting, according to the applicant's opinion, in compliance of the invention with the "Industrial Applicability" ("IA") patentability criterion.

The invention claimed is:

1. A method of preparing a sodium salt of the (2,6-dichlorophenyl)amide of carbopentoxysulfanilic acid having the structure

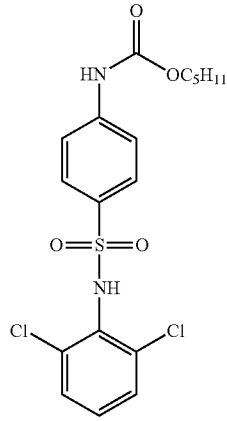

comprising the steps of:
(a) combining 2,6-dichloroaniline and pyridine;
(b) adding carbopentoxysulfanilic acid chloride having the structure

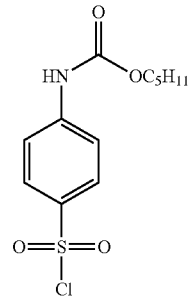

to the mixture of step (a), acidifying the resultant mixture with a solution of hydrochloric acid to a pH of 5 to 5.5, and segregating, washing, and drying a solid precipitate, and
(c) combining the solid precipitate of step (b) with sodium hydroxide in ethyl alcohol solution, removing ethyl alcohol by distillation, followed by isolating and drying the sodium salt of the (2,6-dichlorophenyl)amide of carbopentoxysulfanilic acid as a solid precipitate.

2. The method of claim 1 wherein the overall yield of the sodium salt of the (2,6-dichlorophenyl)amide of carbopentoxysulfanilic acid is 56%.

3. The method of claim 1, wherein the solution of hydrochloric acid is an aqueous solution of hydrochloric acid.

4. The method of claim 1, wherein the carbopentoxysulfanilic acid chloride is added in portions at a temperature of 85° C.

5. The method of claim 1, wherein the mixture of step (b) is stirred at 80° C. for 45 minutes prior to acidifying the mixture with a solution of hydrochloric acid to a pH of 5 to 5.5.

6. The method of claim 5, wherein the mixture is cooled to room temperature after acidifying.

7. The method of claim 1, wherein water is added to the mixture of step (b) prior to acidifying the resultant mixture with a solution of hydrochloric acid to a pH of 5 to 5.5.

8. The method of claim 1, wherein the solid precipitate of step (b) is recrystallized prior to step (c).

* * * * *